United States Patent [19]

Steiner et al.

[11] Patent Number: 5,895,384
[45] Date of Patent: Apr. 20, 1999

[54] DEVICE FOR SHAPING THE CORNEA

[75] Inventors: Rudolf Steiner, Ulm; Richard Leiacker, Neu-Ulm, both of Germany

[73] Assignee: G. Rodenstock Instrumente GmbH, Ottobrunn-Riemerling, Germany

[21] Appl. No.: 08/676,340

[22] PCT Filed: Nov. 22, 1995

[86] PCT No.: PCT/DE95/01629

§ 371 Date: Oct. 7, 1996

§ 102(e) Date: Oct. 7, 1996

[87] PCT Pub. No.: WO96/15742

PCT Pub. Date: May 30, 1996

[30] Foreign Application Priority Data

Nov. 22, 1994 [DE] Germany ................ 44 41 579
Aug. 18, 1995 [DE] Germany ................ 195 30 476

[51] Int. Cl.[6] ................................................ A61B 17/36
[52] U.S. Cl. .................................................. 606/5; 606/4
[58] Field of Search .................................. 606/2, 3, 4, 5, 606/10–12, 6; 351/212

[56] References Cited

U.S. PATENT DOCUMENTS

| | | | |
|---|---|---|---|
| 5,336,216 | 8/1994 | Dewey | 606/4 |
| 5,376,086 | 12/1994 | Khoobehi et al. | 606/4 |
| 5,395,356 | 3/1995 | King et al. | 606/4 |
| 5,461,212 | 10/1995 | Seiler et al. | 606/5 |
| 5,571,107 | 11/1996 | Shaibani et al. | 606/4 |

Primary Examiner—Max Hindenburg
Assistant Examiner—Bryan K. Yarnell
Attorney, Agent, or Firm—Antonelli, Terry, Stout & Kraus, LLP

[57] ABSTRACT

A device for shaping the cornea of an eye, including a laser (1), the laser beam of which has a circular mode of distribution, and a beam-shaping device and a beam-guiding device, which direct the laser beam onto the cornea. To homogenize the energy density over the cross section of the beam, the beam-shaping device is provided with a focusing optic which focuses the laser beam, a diffraction element which is disposed at a short distance from the focus plane of the focusing optic and the diffraction maxima of which interfere with the minima of the mode of distribution, and an image-field diaphragm which is disposed at a site which is optically conjugate to the cornea.

19 Claims, 1 Drawing Sheet

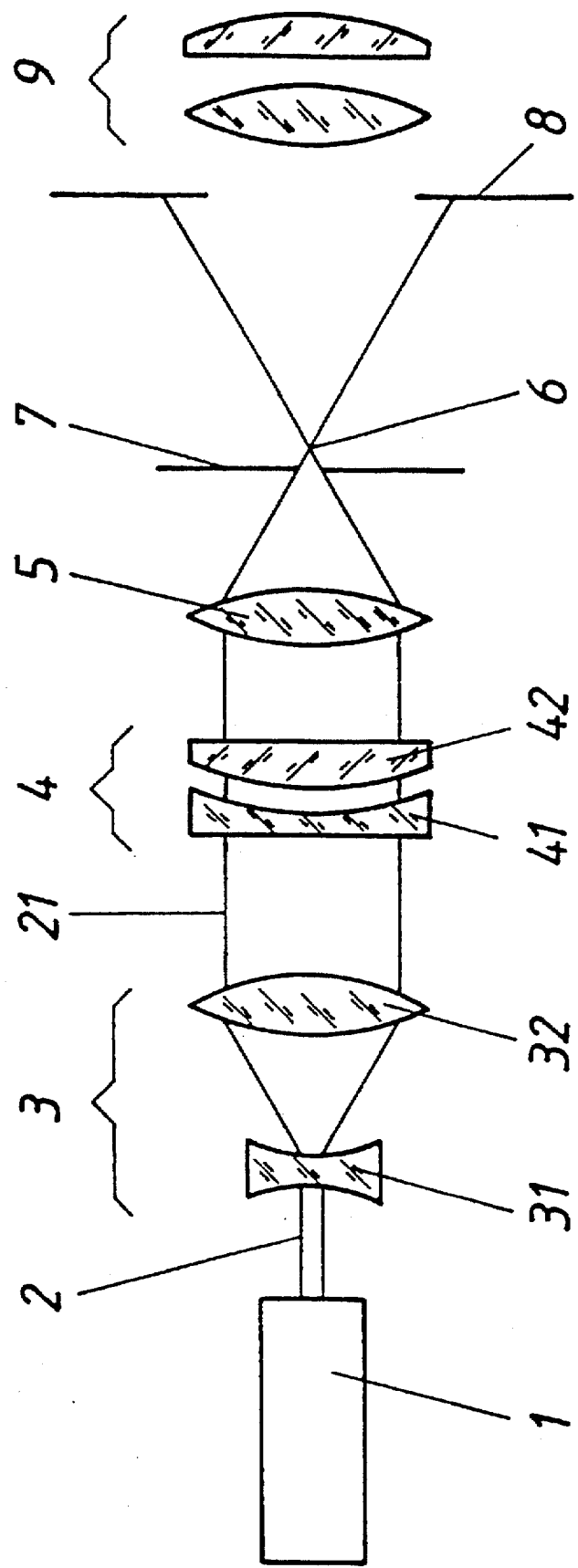

DEVICE FOR SHAPING THE CORNEA

TECHNICAL FIELD

The present invention relates to a device for shaping the cornea according to the generic part of claim 1.

STATE OF THE ART

There are devices for shaping the cornea commerically available using an excimer laser as the laser. Excimer lasers emit light in the UV range, and in ophthalmology, excimer lasers emitting light with a wavelength of 193 nm are often employed.

Light with such a short wavelength can only be shaped and guided with some difficulty in the beam-shaping and beam-guiding device required in cornea laser treatment: for instance, tiny particles of dust on the surface of the lens cause "burnt-in spots" on these lens surfaces.

Furthermore, speculations have been published that light with the aforementioned wavelengths may be carcinogenic and/or mutagenic.

For this reason, it was proposed some time ago to use lasers emitting light in the infrared spectral range with wavelengths of about 3 μm in the respective applications instead of excimer lasers, because water in this spectral range has a strong absorption band. Most of the lasers emitting in this spectral range are YAG lasers, the laser beam of which has a cicular mode of distribution. In order that the circular mode of distribution is not imaged as a "circular" cornea ablation, it is necessary that in the devices for shaping the cornea on which the generic part of claim 1 is based, the energy density is homogenized over the cross section of the beam.

A relatively complicated beam-shaping device for excimer lasers, not having a circular mode of distribution, in which a light guide having an oblong cross section is used, is known from DE-A-40 04 423.

DESCRIPTION OF THE INVENTION

The object of the present invention is to provide a device for shaping the cornea according to the generic part of claim 1 in such a manner that a homogeneous laser beam is placed at disposal with simple means even if using a laser having a circular mode of distribution.

An element of the present invention is that the beam-shaping device for homogenizing the energy density over the cross section of the beam is provided with a focusing optic, which focuses the widened laser beam, a diffraction element, which is disposed at a short distance from the focus plane of the focusing optic and the diffraction maxima of which interfere with the minima of the mode of distribution, an image-field diaphragm, which is disposed at a site which is optically conjugate to the cornea.

The diffraction element is made respectively disposed in the beam path in such a manner that its diffraction maxima interfere at the site of the image-field diaphragm with the minima of the mode structure. In this way, the energy density can be homogenized with simple means over the beam cross section. Moreover, the beam-shaping device can be easily adapted to the radial distribution of the mode structure different from laser to laser by moving the diffraction element in a direction on the optical axis.

The diaphragm provided for delimiting the image field is disposed in the plane of the beam homogenization and is imaged via a (further) optic onto the cornea. In other words, the image-field diaphragm is optically conjugate to the cornea. (Optically conjugate values refer, in accordance with the prevailing definition, to values which are disposed in pairs, in that one value relates to the object respectively the object space and the other value relates to the image respectively the image space.)

Various elements can be utilized as diffraction elements. Two possibilities, in which the use of an aperture diaphragm has cost advantages compared to the use of a grid, are described in claim 2.

In a preferred embodiment of the present invention, an expansion optic is provided before the focusing optic which widens the laser beam. In this way, the diameter of the laser beam is widened (approximately) to the diameter value or a larger value, as is required for shaping the cornea in such a manner that all "beam manipulations" can be executed at the "exactly required beam cross section" or at a larger beam cross section then with greater accuracy.

This is especially advantageous in the invented improvement of the present invention described in claim 4: According to this claim, a radial-forming element composed of a plano-concave and a plano-convex lens, whose concave and convex surfaces face each other, is provided for setting a radial distribution of the energy of the laser beam set according to the desired cornea ablation.

According to claim 6, it is preferable if the refractive indices of both lenses are the same and the absorption of these two elements varies according to the laser beam wavelength. By way of illustration, acording to the correction of myopia, the concave lens has to have the greater absorption respectively has to be composed of a material having a higher absorption coefficient.

The lenses, of which the radial-forming element is composed, can be made inexpensively on devices, such as those common for the manufacture of ophthalmic lenses.

The further improvement of the present invention characterized in claims 5 and (optionally) 6 represents a particularly simple solution, compared to the known solutions, for influencing the energy distribution according to the desired cornea ablation, permitting inexpensive adaption to the required ablation profile, for the respective correction of the individual vision defect.

In particular, this invented solution for setting the radial profile has the advantage that also not rotational symmetrical beam profiles can be set, like those needed, by way of illustration, to correct astigmatism.

The radial-forming element and, in particular, the element designed according to the present invention can, according to claim 7, be disposed between the lenses of the expansion optic or, according to claim 8, after the image-field diaphragm in the beam guiding device.

Especially advantageous however is if the radial-forming element according to claim 9 is disposed at the site of the image-field diaphragm or a site which is optically conjugate thereto, because the radial beam energy is homogeneous and constant at the site of the image-field diaphragm.

On the other hand, at the site of the image-field diaphragm the beam diameter is, corresponding to the diameter of the area of the cornea to be ablated, only 5 to 7 mm, unless working with a beam of an enlarged diameter. If the radial forming occurs solely by means of absorption, lens elements with a strong curvature have to be employed.

For this reason, it is especially advantageous if the beam shaping occurs not only by means of absorption of the lens elements, but in addition also by means of scattering. The scattering particles, such as by way of illustration titanium oxide, can intensify the drop in radial energy via the concentration of the admixture, because scattering increases exponentially with depth corresponding to the scattering incidents per unit of length. Moreover, the scattering characteristic can be influenced by means of the size of the scattering particles, with the scattering characteristic being able to change from strong forward scattering to isotropic scattering.

Scattering can be generated by a medium having low absorption properties, to which the scattering particles are added, being enclosed in a chamber. The chamber can, by way of illustration, be composed of a quarz material. As a medium having low absorption properties, for instance, liquid silicon to which the scattering particles are added can be employed. Finally the medium is polymerized. Naturally, other polymers which are not ablated by the laser wavelength can be used instead of silicon. However, the use of silicon is preferred, because silicon has a refractive index similar to quarz.

The use of scattering particles has the additional advantage that irregularities in the energy distribution caused by the mode structure are additionally homogenized by the scattering processes. This is comparable to the known milk-glass effect.

The scattering chamber should also be disposed as close as possible to the site of the image-field diaphragm. The desired laser energy for cornea ablation can be set by the selection of the aperture of the imaging optic and the selection of the scattering geometry of the particles as well as the selection of their concentration.

Any laser having a circular mode of distribution can be employed as the treatment laser as long as it emits light only in the spectral range suited for shaping the cornea by means of corresponding cornea ablation. These are, i.a., all lasers that emit light between approximately 2.7 μm and 3.3 μm. An especially suited laser is the erbium-YAG laser mentioned in claim 17. The present invention is, of course, not limited to the aforementioned wavelength range.

Described in the previous section have been the essential elements needed for realizing the present invention respectively invented further improvements thereof, for which, if need be, independent protection shall be applied. This applies, in particular, to the beam-shaping elements using scattering particles as claimed in claims 10 to 16.

The invented device can, of course, be provided with other elements:

For instance, according to claim 18, the beam-guiding device can be provided with a further optic which directs the laser beam onto the eye to be treated. This further optic perferably has the same focal length as the focusing optic (claim 19).

BRIEF DESCRIPTION OF THE DRAWING

The present invention is made more apparent by way of example in the following, without the intention of limiting the scope or spirit of the overall inventive idea, using preferred embodiments with reference to the single figure of the drawing to which reference is explicitly made for the disclosure of all invented details not explained more closely herein:

This FIGURE shows a longitudinal section of the invented device.

DESCRIPTION OF THE PREFERRED EMBODIMENT

The invented apparatus is provided with a laser 1 which emits a laser beam 2, the wavelength of which is suited to ablate the (not depicted) cornea of a human eye. The wavelength of laser beam 2 can, in particular, be in the 3 μm range. A suited laser is, by way of illustration, a Er:YAG laser having a wavelength of approximately 3 μm. Usually lasers emitting light in this wavelength range have a circular mode of distribution. This is particularly the case of YAG lasers such as the previously mentioned Er:YAG laser.

An expansion optic 3 which widens laser beam 2 from a diameter of usually 4 . . . 6 mm to a diameter of approximately 25 . . . 40 mm (reference No. 21) is provided in the beam path of laser 1. For this purpose, the expansion optic 3 is provided with an element 31 having negative refractive power and an element 32 having positive refractive power, which do not necessarily need to be single lenses, as shown in the figure.

A radial-forming element 4 used for setting the radial distribution of the energy of the laser beam 3 set according to the desired cornea ablation is provided in the beam path 21 following the expansion optic. In the shown preferred embodiment, element 4 is composed of a plano-concave and a plano-convex lens 41 respectively 42, the concave respectively convex surfaces of which face each other. The two lenses 41 and 42 have (approximately) the same refractive indices, however, different absorptions for the wavelength of laser beam 2 so that the desired energy distribution is (practically) obtained over the cross section of, in the shown preferred embodiment parallel, beam 21 without influencing "the course of the beam".

A suited combination of materials for lenses 41 and 42 is (by way of illustration) quarz/quarz-infrasil, IRG3/LaSF9, IRG9/FK52 or, preferably, IRG7/LF8. The names are the ones used by Schott, Mainz, Germany. Other combinations of materials are, of course, also possible.

In addition, beam shaping can occur not only by means of absorption of lenses 41 and 42, but also by means of scattering. The scattering particles, such as by way of illustration titanium oxide, can intensify the drop in radial energy via the concentration of the admixture, because scattering increases exponentially with depth corresponding to the scattering incidents per unit of length. Moreover, the scattering characteristic can be influenced by means of the size of the scattering particles, with the scattering characteristic being able to change from strong forward scattering to isoptropic scattering. The use of scattering particles has the advantage that irregularities in the energy distribution caused by the mode structure can be additionally homogenized by the scattering processes. This can be compared with the known milk glass effect.

In any case, by means of a suited selection of the thickness and the material properties of the lenses and the curvatures of the surfaces facing each other of the two lenses, the widened beam 21 can be given the profile which generates the desired radius-dependent and azimuth angle-dependent energy distribution of the laser beam. In this way, spherical as well as astigmatic vision errors of the eye can be corrected. The use of aspherical surfaces with lenses 41 and 42 is, of course, also possible so that aspherical ablation occurs.

In the shown preferred embodiment, a focusing optic 5 which focuses the widened laser beam 21 in a focal point 6 is provided after the radial-forming element 4 in the light path. The focusing optic usually has a focal length of 20 mm.

A diffraction element 7 whose diffraction maxima interfere with the minima of the mode distribution is provided at a distance of, by way of illustration, 4 to 5 mm before the focal point 6. In the preferred embodiment the diffraction element 7 is an aperture diaphragm having an aperture diameter of less than 1 mm, for instance 0.8 mm.

Furthermore, an image-field diaphragm 8, usually having a diameter of 7 mm, is disposed at a site which is optically conjugate to the cornea. A further optical system 9, which in particular can have the same focal length as the focusing optic 5, is provided after the image-field diaphragm 8, resulting in 1:1 imaging by the image-field diaphragm

What is claimed is:

1. A device for shaping the cornea of an eye, said device comprising:

a laser for providing a laser beam having a circular mode of distributions;

a beam-shaping devices, including a focusing optic for focusing the laser beam at a focus plane, and a diffraction element disposed closely adjacent the focus plane of said focusing optic, and having diffraction maxima which interfere with minima of the mode of distribution, for homogenizing energy density of the laser beam over a cross section of the beam; and a beam-guiding device, including an image-field diaphragm disposed optically conjugate to the cornea, for directing the laser beam onto the cornea.

2. A device according to claim 1, wherein said diffraction element comprises a grid or an aperture diaphragm.

3. A device according to claim 1 or 2, wherein said beam-shaping device further includes an expansion optic for widening the laser beam before the laser beam is focused by said focusing optic.

4. A device according to claim 3, wherein said beam-shaping device further includes a radial-forming element for setting a radial distribution of energy of the laser beam according to a desired ablation.

5. A device according to claim 4, wherein said radial-forming element comprises a plano-concave lens and a plano-convex lens, a concave surface of said plano-concave lens and a convex surface of said plano-convex lens facing each other.

6. A device according to claim 5, wherein said plano-concave lens and said plano-convex lens have identical refractive indices and different absorptions for a wavelength of said laser beam.

7. A device according to claim 4, wherein said expansion optic includes a Plurality of lenses, and said radial-forming element is disposed between said lenses of said expansion optic or after said expansion optic.

8. A device according to claim 4, wherein said radial-forming element is disposed after said image-field diaphragm.

9. A device according to claim 4, wherein said radial-forming element is disposed after said image-field diaphragm or at a site which is optically conjugate thereto.

10. A device according to claim 1, wherein said beam-shaping device further includes a radial-forming element provided with scattering particles.

11. A device according to claim 10, wherein said scattering particles are enclosed in a polymer.

12. A device according to claim 11, wherein said polymer is enclosed in a quartz chamber.

13. A device according to claim 10 or 11, wherein said polymer is a silicone polymer.

14. A device according to claim 10 or 11, wherein said scattering particles comprise titanium. oxide.

15. A device according to claim 10, wherein said scattering particles are of a size selected according to a desired scattering characteristic.

16. A device according to claim 10, wherein said scattering particles are disposed in a region of said image-field diaphragm.

17. A device according to claim 1, wherein said laser comprises an erbium-YAG laser.

18. A device according to claim 1, wherein said beam-guiding device further includes an optical system disposed after said image-field diaphragm.

19. A device according to claim 18, wherein said optical system has a focal length the same as that of said focusing optic.

* * * * *